United States Patent [19]
Ise

[11] Patent Number: 5,380,526
[45] Date of Patent: Jan. 10, 1995

[54] ANTIDIABETIC AGENT AND METHOD OF TREATING DIABETES

[75] Inventor: Michihito Ise, Kawagoe, Japan

[73] Assignee: Kureha Chemical Industry Co., Ltd., Japan

[21] Appl. No.: 220,869

[22] Filed: Mar. 31, 1994

[30] Foreign Application Priority Data

Apr. 14, 1993 [JP] Japan .................................. 5-110882

[51] Int. Cl.⁶ ............................................ A01N 59/00
[52] U.S. Cl. ...................................... 424/125; 514/866
[58] Field of Search ......................... 514/866; 424/125

[56] References Cited

U.S. PATENT DOCUMENTS 4,681,764  7/1987  Endo et al. ......................... 424/125

*Primary Examiner*—Marianne M. Cintins
*Assistant Examiner*—Keith MacMillan
*Attorney, Agent, or Firm*—Parkhurst, Wendel & Rossi

[57] ABSTRACT

An antidiabetic agent containing a spherical carbon (e.g., an activated spherical carbon or a spherical carbonaceous adsorbent) as an active ingredient. The antidiabetic agent can be used for treating diabetes, preferably by using the agent internally as an oral medicine and will not be painful to a patient at an injection site, unlike conventional injections of insulin. Moreover, unlike conventional antidiabetic agents, the antidiabetic agent of the present invention will not induce hypoglycemia.

11 Claims, No Drawings

ANTIDIABETIC AGENT AND METHOD OF TREATING DIABETES

BACKGROUND OF THE INVENTION

1. Field of the Invention

The present invention relates to an antidiabetic agent containing a spherical carbon as an active ingredient and a method of treating diabetes using that antidiabetic agent.

2. Description of the Related Art

The affliction "diabetes" encompasses both (1) primary diabetes, which is mainly induced by hereditary causes and which primarily causes insulin deficiency, and (2) secondary diabetes, which is induced by acquired causes. A common symptom of the two types of diabetes is hyperglycemia, which causes complications such as neuropathy or retinopathy. As these complications progress, they result in deuteropathies such as serious infection, sudden death, blindness, heart failure, cerebral infarction, myocardial infarction, and the like. Therefore, sufficient care must be given to chronic complications.

Insulin and internal antidiabetics such as sulfonylurea agents and biguanide agents are conventionally used as antidiabetics.

However, insulin is completely ineffective when administered internally, and is nowadays clinically administered only as an injection, which is painful to the patient. In addition to the pain, there sometimes occur redness, swelling, induration, itching, and the like at the site of the injection. Further, repeated subcutaneous injections at the same site sometimes cause lipodystrophy such as atrophy or hypertrophy of subcutaneous fat. Hypoglycemia may also occur as a serious side effect of taking insulin. Specifically, sufficient care should be taken not to cause hypoglycemia due to over-injection. Careful administration is required for the patient or the condition which is liable to suffer from hypoglycemia.

The above internal antidiabetics cannot completely be substituted for insulin. For example, insulin is indispensable for, and the antidiabetics have no effect on, diabetic conditions such as diabetic coma, juvenile diabetes, diabetes with ketoacidosis and serious infection.

Medicines of the sulfonylurea agent group include tolbutamide, chlorpropamide, acetohexamide, tolazamide, glibenclamide, etc., all of which sometimes cause serious and delayed hypoglycemia and, thus, must be carefully administered.

Medicines of the biguanide agent group include buformin, metformin, etc., which sometimes cause serious lactic acidosis or hypoglycemia and, thus, must be carefully administered.

SUMMARY OF THE INVENTION

It is an object of the present invention to provide an antidiabetic agent containing a spherical carbon as an active ingredient.

It is another object of the present invention to provide a method of treating diabetes that avoids the problems caused by insulin injections and conventional antidiabetics.

The present inventor thoroughly investigated an active antidiabetic ingredient different from insulin or conventional internal antidiabetics such as sulfonylurea agents and biguanide agents. As a result of that thorough investigation, the present inventor has discovered that the serum glucose values of diabetic rats are decreased by orally administering a spherical carbon to the rats. The present invention is based on this finding.

In order to achieve the objects of the present invention, there is provided an antidiabetic agent comprising a spherical carbon as an active ingredient.

The present invention further provides a method of treating diabetes that avoids the problems caused by insulin injections and conventional antidiabetics.

DETAILED DESCRIPTION OF THE PREFERRED EMBODIMENTS

The spherical carbon used as an active ingredient in the present invention is not particularly limited as long as it constitutes an activated carbon having a spherical shape that can be used for medical treatment. Although a medical activated carbon powder is generally useful as an antidote, it is liable to cause constipation as a side effect, particularly when the carbon powder is used continually. This is a critical problem because constipation at the time of illness is dangerous.

The spherical carbon used in the present invention has a particle diameter ranging from 0.05 to 2 mm. When the diameter is less than 0.05 mm, side effects such as constipation and the like are not sufficiently eliminated. On the other hand, when the diameter is over 2 mm, oral administration of the spherical carbon becomes difficult, and the desired pharmacological effect does not appear quickly.

The shape of the spherical carbon is an important factor for obtaining satisfactory medical effects of the present invention. It is therefore necessary that the spherical carbon used in the present invention has a substantially spherical shape.

Any raw materials used for producing the spherical carbon may be used for producing the spherical carbon employed in the present invention. Although examples of such raw materials include sawdust, coals, coconut shells, petroleum pitches, coal pitches, and synthetic organic high polymers, petroleum hydrocarbons are preferred. In the present invention, it is preferred to use an activated spherical carbon and/or a spherical carbonaceous adsorbent as the spherical carbon.

Particles of an activated spherical carbon that can be used in the present invention have a diameter of 0.05 to 2 mm. A basic method of producing the activated spherical carbon used in the present invention involves forming a raw material into fine spherical particles, carbonizing the spherical particles, and then activating the carbonized particles.

Various activation methods can be carried out, for example, using steam, chemicals, air, or carbon dioxide. The activated spherical carbon particles can be produced by, for example, the following three methods: The first method comprises forming a raw material powder into fine spherical particles using a binder such as pitch, carbonizing the particles by baking the particles in an inert atmosphere at 600° to 1000° C., and then activating the carbonized particles in an atmosphere of steam at 850° to 1000° C. The second method comprises forming melted pitch into fine spherical particles, oxidizing the particles in an atmosphere containing oxygen to render the particles infusible, and then carbonizing and activating the infusible particles under the same conditions as those in the first method, as disclosed in, for example, Japanese Patent Publication No. 51-76 (see U.S. Pat. No. 3,917,806). The third method comprises melt-extruding pitch to form a string-like pitch, breaking the string-like pitch, casting the broken product into hot water to obtain spherical particles, oxidizing the particles in an atmosphere containing oxygen to render the particles infusible, and then carbonizing and activating the infusible particles under the same conditions as those in the first method, as disclosed in, for example, Japanese Patent Publication No. 59-10930 (see U.S. Pat. No. 4,420,443).

The spherical carbonaceous adsorbent used in the present invention preferably comprises activated carbon particles having a diameter of 0.05 to 2 mm, a pore radius of not more than 80 angstroms in a pore amount of 0.2 to 1.0 ml/g, a total amount of acidic groups (A) of 0.30 to 1.20 meq/g, a total amount of basic groups (B) of 0.20 to 0.70 meq/g, and a ratio of the total amount of acidic groups (A)/total amount of basic groups (B) of 0.40 to 2.5. An example of these spherical carbonaceous adsorbents is disclosed in Japan Patent Publication No. 62-11611 (see the specification of U.S. Pat. No. 4,681,764).

The spherical carbonaceous adsorbent used in the present invention can be produced by further oxidizing and reducing, at a high temperature, activated spherical carbon particles having a diameter of 0.05 to 2 mm and a pore radius of not more than 80 angstroms in a pore amount of 0.2 to 1.0 ml/g. Oxidation and reduction at a high temperature are preferably effected so that the total amount of acidic groups (A) and the total amount of basic groups (B) of the spherical carbonaceous adsorbent obtained are adjusted within the ranges of 0.30 to 1.20 meq/g and 0.20 to 0.70 meq/g, respectively, and the ratio of the total amount of acidic groups (A)/total amount of basic groups (B) is adjusted within the range of 0.40 to 2.5.

The total amount of acidic groups (A) and the total amount of basic groups (B) are determined by the following usual methods:

(a) Total amount of acidic groups (A)

One gram of a pulverized adsorbent specimen that passed thorough a Taylor standard sieve of 200 mesh is added to 50 ml of 0.05N aqueous NaOH solution, followed by shaking for 48 hours. The resultant mixture is filtered to remove the adsorbent, and the filtrate is neutralized by titration. The total amount of acidic groups (A) is determined by the amount of NaOH consumed by the titration and is expressed in units of meq/g of specimen.

(b) Total amount of basic groups (B)

One gram of a pulverized adsorbent specimen that passed thorough a Taylor standard sieve of 200 mesh is added to 50 ml of 0.05N aqueous HCl solution, followed by shaking for 24 hours. The resultant mixture is filtered to remove the specimen, and the filtrate is neutralized by titration. The total amount of basic groups (B) is determined by the amount of HCl consumed by the titration and is expressed in units of meq/g of specimen.

High temperature oxidation is performed by heating the particles at a high temperature in an oxidizing atmosphere containing oxygen, which is formed by using pure oxygen, nitrogen oxides, or air as an oxygen source.

High temperature reduction is performed by heating the particles at a high temperature in an atmosphere of a gas that is inert to carbon. The atmosphere of a gas that is inert to carbon is formed by using nitrogen, argon, helium, or a mixture thereof.

Oxidative heating is preferably carried out at 300° to 700° C., more preferably at 400° to 600° C., in an atmosphere preferably containing 0.5 to 25% by volume of oxygen, more preferably 3 to 10% by volume of oxygen. Reduction is preferably carried out at 700° to 1100° C., more preferably 800° to 1000° C., in an atmosphere of nitrogen.

The present inventor orally administered the above spherical carbonaceous adsorbent to diabetic rats that had already been administered with streptozotocin. As a result, the inventor found the surprising phenomenon that serum glucose values of the rats decreased. It was thus found that a medicine containing as an active ingredient the spherical carbon is useful as an antidiabetic agent. As a matter of course, this medicine is useful for treating the chronic complications of diabetes, such as retinopathy or neuropathy, which are caused by hyperglycemia. In addition, importantly, when the antidiabetic agent of the present invention was administered to normal rats, no abnormality was induced, and hypoglycemia did not occur.

The antidiabetic agent of the present invention can preferably be administered orally. The dosage depends on the subject (animal or human), the age of the subject, differences among subjects, the conditions of the disease, etc. For example, the oral dosage of the spherical carbon for a human patient is generally within the range of 0.2 to 20 g per day. The dosage may be administered at one time or in 2 to 4 portions. The daily dosage may be adjusted appropriately according to symptoms.

Thus, the spherical carbon can be administered as it is or in the form of a pharmaceutical composition as an antidiabetic agent.

When the spherical carbon particles are used as they are, it is most convenient to ingest a pharmaceutically acceptable aqueous slurry in which the particles are dispersed in drinking water.

The spherical carbon particles may be administered as a medicine to patients in any desired form such as granules, tablets, sugar-coated tablets, capsules, stick packages, divided packages, suspensions, or the like.

When the particles are administered in the form of capsules, ordinary gelatin capsules or, if necessary, enteric capsules may be used. When the carbon particles are used in the form of granules, tablets, or sugar-coated tablets, the form must be disintegrated into the original fine spherical particles in the alimentary canal of a patient.

Although the content of the spherical carbon in a pharmaceutical composition forming part of the present invention may be varied according to symptoms and other factors, the content is usually 1 to 100% by weight, preferably 10 to 99% by weight.

A pharmaceutical composition for diabetes may comprise the spherical carbon as it is in a dosage unit form such as a capsule, a stick package, or a divided package. That is, the spherical carbon particles as they are may be enclosed in a capsule or a container such as a stick or a divided bag, and the adsorbent particles are administered in the form of capsules, stick packages, or divided packages to a patient suffering from diabetes.

The antidiabetic agent of the present invention can be used for treating diabetes, preferably by administering the agent internally as an oral medicine. Therefore, unlike insulin, which has to be injected, the antidiabetic agent of the present invention will not give a patient pain. Further, the antidiabetic agent of the present invention will not induce hypoglycemia and, thus, does not have the problem of conventional antidiabetics, which are liable to induce hypoglycemia.

Although the present invention will be more precisely explained below with reference to the following examples, the scope of the present invention is not limited thereto.

PRODUCTION EXAMPLE 1

Preparation of a Spherical Carbonaceous Adsorbent

An autoclave equipped with a stirrer was charged with 100 g of naphthalene and 300 g of pitch (H/C=0.55, flow point 220° C.) having an anisotropic region that was not localized under a polarization microscope. The resultant mixture was mixed well at 180° C. to form a solution. Into the resulting solution, 1200 g of 0.5 % aqueous polyvinyl alcohol solution was added. Then, the mixture was vigorously stirred at 140° C. for 30 minutes and cooled to room temperature under stirring to form a dispersion of spherical particles. After a large part of the water was separated from the dispersion, the remaining spherical particles were treated with hexane in an extractor to remove the naphthalene contained therein by extraction and then dried by air flow. The thus-obtained particles were then heated to 300° C. at a rate of 25° C./h by a flow of heated air in a fluidized bed system, and were further maintained for 2 hours at 300° C. to obtain infusible oxygen-containing spherical particles. The particles were then heated to 900° C. in steam and kept at 900° C. for 2 hours in steam so as to carbonize and activate the particles to obtain porous activated spherical carbon. The activated spherical carbon had a diameter of 0.05 to 1.0 mm and a pore radius of not more than 80 angstroms in a pore amount of 0.755 ml/g, which was determined by a methanol adsorption method using an automatic adsorption measuring apparatus.

The thus-obtained activated spherical carbon particles were heated to 600° C. in an atmosphere containing 3% by volume of oxygen, and were further heated at 600° C. for 3 hours in the same atmosphere using a fluidized bed. Then, the particles were further heated to 950° C. in an atmosphere of nitrogen and kept at 950° C. for 30 minutes in the same atmosphere to obtain an intended spherical carbonaceous adsorbent (hereinafter referred to as "Sample 1").

The spherical carbonaceous adsorbent particles had a diameter of 0.05 to 1 mm, a pore radius of not more than 80 angstroms in a pore amount of 0.751 ml/g, which was determined by the methanol adsorption method using an automatic adsorption measuring apparatus, a total amount of acidic groups (A) of 0,542 meg/g, a total amount of basic groups (B) of 0.525 meq/g, and a ratio of the total amount of acid groups (A)/total amount of basic groups (B) of 1.03.

In acute toxicity tests of the spherical carbonaceous adsorbent, which was orally administered to male and female rats (Cpb: WU: Wistar Random), no abnormality was observed even at the maximum dosage (5000 mg/kg for male and female rats>based on the Guidelines for Toxicity Studies of Drugs (Notification No. 118 of the Pharmaceutical Affairs Bureau, Ministry of Health and Welfare, Japanese Government, February 15, 1984).

EXAMPLE 1

Effect of Antidiabetic Agent on Diabetic Rats

Sample 1 obtained in Production Example 1 was used as the spherical carbonaceous adsorbent functioning as an active ingredient of the antidiabetic agent.

According to the ordinary method of preparing a diabetic model, streptozotocin (41 mg/kg (rat body weight)) was administered to the caudal veins of male JCL-SD rats (body weight ranging from 200 to 230 g) to prepare diabetic model rats. After ten days had elapsed following the administration of streptozotocin, blood was collected from the jugular vein of each rat in the morning, serum was separated, and the serum glucose value was measured. The rats were then divided into two groups (a control group and an administration group; 6 rats each) so that there was no deviation between the groups.

The control group and the administration group were freely fed on rat feed (produced by Japan CLEA) and rat feed (produced by Japan CLEA) having added thereto 5% spherical carbonaceous adsorbent, respectively, for 6 weeks.

After 4 and 6 weeks had passed, blood was collected from the jugular vein of each rat in the morning, serum was separated, and the serum glucose value was measured. The results are shown in Table 1. As seen from Table 1, although the serum glucose values of the rats in the control group increased, all serum glucose values of the rats in the administration group decreased. This decrease in the serum glucose value suggests that abnormal metabolism is corrected.

TABLE 1

|  | At the Start Serum glucose value (mg/dl) | body weight (g) | After an elapse of 4 weeks Serum glucose value (mg/dl) | After an elapse of 6 weeks Serum glucose value (mg/dl) |
| --- | --- | --- | --- | --- |
| Control group | 454 ± 47 | 297 ± 7 | 573 ± 81 | 558 ± 68 |
| Administration group | 468 ± 35 | 297 ± 12 | 341 ± 124 | 344 ± 142 |
| Significant difference |  |  | p < 0.01 | p < 0.01 |

Value: Mean ± Standard deviation (n = 6)
Significant difference test: Non-pair t-test

EXAMPLE 2

Effect of Antidiabetic Agent on Normal Rats

Sample 1 was used as the spherical carbonaceous adsorbent as in Example 1.

Male JCL-SD rats were weighed and divided into two groups (a control group and an administration group; 8 rats each) so that there was no deviation in body weight between the groups.

The control group and the administration group were freely fed on rat feed (produced by Japan CLEA) and rat feed (produced by Japan CLEA) having added thereto 5% spherical carbonaceous adsorbent, respectively, for 4 weeks.

After 4 weeks had passed, blood was collected from the jugular vein of each rat in the morning, and the serum glucose value was measured. The results are shown in Table 2. As seen from Table 2, the spherical carbonaceous adsorbent did not induce hypoglycemia in the normal rats.

TABLE 2

| | Serum glucose value (mg/dl) |
|---|---|
| Control group | 213 ± 8 |
| Administration group | 215 ± 11 |
| Significant difference | NS |

Value: Mean ± Standard deviation (n = 8)
Significant difference test: Non-pair t-test

FORMULATION EXAMPLE 1

Capsule

Two hundred milligrams of spherical carbonaceous adsorbent obtained in Production Example 1 were enclosed in a gelatin capsule to form a capsule.

FORMULATION EXAMPLE 2

Stick Package

Two grams of spherical carbonaceous adsorbent obtained in Production Example 1 were put into a stick made of a laminated film (constitution = glassine paper/polyethylene/aluminum foil/polyethylene/polyvinylidene chloride; thickness = 74±8 μm) and was heat-sealed to produce a stick package.

What is claimed is:

1. A method of treating diabetes without producing side effects comprising administering a substantially spherical carbon in a diabetes-treating effective amount to a patient suffering therefrom.

2. The method of claim 1, wherein said spherical carbon is an activated spherical carbon.

3. The method of claim 1, wherein said spherical carbon is a spherical carbonaceous adsorbent.

4. The method of claim 1, wherein said spherical carbon has a particle diameter of about 0.05 mm to about 2 mm.

5. The method of claim 2, wherein said spherical carbon is activated with steam.

6. The method of claim 3, wherein said spherical carbonaceous adsorbent has a particle diameter of from about 0.05 to about 2 mm.

7. The method of claim 6, wherein said spherical carbonaceous adsorbent has a pore radius of less than 80 angstroms in a pore amount of about 0.2 to about 1.0 ml/g.

8. The method of claim 7, wherein said spherical carbonaceous adsorbent has a total amount of acidic groups (A) of about 0.30 to about 1.20 meq/g, a total amount of basic groups (B) of about 0.20 to about 0.70 meq/g, and a ratio of the total amount of acidic groups (A): total amount of basic groups (B) within the range of about 0.40:1 to about 2.5:1.

9. The method of claim 1, wherein said spherical carbon is administered orally.

10. The method of claim 9, wherein said spherical carbon is administered in an amount of about 0.2 to 20 g per day.

11. The method of claim 1, wherein said spherical carbon is administered in an amount of about 0.2 to 20 q per day.

* * * * *

UNITED STATES PATENT AND TRADEMARK OFFICE
CERTIFICATE OF CORRECTION

PATENT NO. : 5,380,526
DATED      : January 10, 1995
INVENTOR(S): Michihito ISE

It is certified that error appears in the above-identified patent and that said Letters Patent is hereby corrected as shown below:

In column 4, line 2, change "400 ©" to --400°--.

In column 5, line 55, change "0,542" to --0.542--;

In column 5, line 64, change ">" to --)--.

In the claims, column 8, claim 11, line 30, change "q" to --g--.

Signed and Sealed this

Thirteenth Day of June, 1995

Attest:

BRUCE LEHMAN

*Attesting Officer*     *Commissioner of Patents and Trademarks*